United States Patent
Kruse et al.

(10) Patent No.: US 8,523,740 B2
(45) Date of Patent: Sep. 3, 2013

(54) METHOD AND APPARATUS FOR PROVIDING COMMUNICATIONS WITH HAPTIC CUES

(75) Inventors: Barbara Kruse, San Francisco, CA (US); George V. Anastas, San Carlos, CA (US); Neil Olien, Montreal (CA); Ryan Steger, Sunnyvale, CA (US)

(73) Assignee: Immersion Corporation, San Jose, CA (US)

( * ) Notice: Subject to any disclaimer, the term of this patent is extended or adjusted under 35 U.S.C. 154(b) by 0 days.

(21) Appl. No.: 13/405,845

(22) Filed: Feb. 27, 2012

(65) Prior Publication Data

US 2012/0212340 A1 Aug. 23, 2012

Related U.S. Application Data

(63) Continuation of application No. 11/966,624, filed on Dec. 28, 2007, now Pat. No. 8,123,660.

(51) Int. Cl.
*A63B 24/00* (2006.01)

(52) U.S. Cl.
USPC ........................................ 482/3; 482/1; 482/8

(58) Field of Classification Search
USPC ................. 482/1–9, 900–902; 434/247, 258; 715/700, 733, 744; 345/156; 340/407.1, 340/407.2; 600/594

See application file for complete search history.

(56) References Cited

U.S. PATENT DOCUMENTS

| | | | |
|---|---|---|---|
| 4,570,927 A * | 2/1986 | Petrofsky et al. | 482/60 |
| 5,679,004 A * | 10/1997 | McGowan et al. | 434/247 |
| 6,368,251 B1 * | 4/2002 | Casler et al. | 482/4 |
| 6,424,333 B1 | 7/2002 | Tremblay et al. | |
| 6,781,569 B1 * | 8/2004 | Gregorio et al. | 345/157 |
| 6,842,877 B2 | 1/2005 | Robarts et al. | |
| 7,082,570 B1 | 7/2006 | Von Wiegand et al. | |
| 7,137,069 B2 | 11/2006 | Abbott et al. | |
| 7,413,528 B2 * | 8/2008 | Nestler | 482/52 |
| 8,083,693 B1 * | 12/2011 | McKeon et al. | 600/594 |
| 2006/0293151 A1 * | 12/2006 | Rast | 482/8 |
| 2007/0244641 A1 * | 10/2007 | Altan et al. | 701/300 |
| 2009/0325766 A1 * | 12/2009 | Kasama et al. | 482/8 |

* cited by examiner

*Primary Examiner* — Glenn Richman

(74) *Attorney, Agent, or Firm* — Pillsbury Winthrop Shaw Pittman LLP

(57) ABSTRACT

A method and apparatus of generating haptic cues for pacing and monitoring are disclosed. After sensing an event via a component, a process for generating haptic cues generates an input in response to the event. The component, in one example, may be a sensor or a combination of a sensor and a haptic actuator. Upon receipt of the input, the process retrieves a haptic signal from a tactile library in response to the input. A haptic feedback in response to the haptic signal is subsequently generated.

35 Claims, 5 Drawing Sheets

METHOD AND APPARATUS FOR PROVIDING COMMUNICATIONS WITH HAPTIC CUES

CROSS-REFERENCE TO RELATED APPLICATIONS

This application is a continuation of U.S. patent application Ser. No. 11/966,624, filed Dec. 28, 2007, and issued as U.S. Pat. No. 8,123,660 on Feb. 28, 2012, which is incorporated herein by reference in its entirety.

FIELD

The exemplary embodiment(s) of the present invention relates to the field of electronic communications. More specifically, the exemplary embodiment(s) of present invention relates to communications using haptic feedbacks.

BACKGROUND

As computer-based systems, such as monitoring systems, training systems, game consoles, appliances, personal computers ("PCs"), servers, personal digital assistants ("PDAs"), cellular phones, become more prevalent in recent years, intuitive human-machine communications have become increasingly important. Human-machine communications generally can be categorized into user interface device and machine interface device, wherein user interface device provides a mechanism for a user to talk to a machine while machine interface device is a mechanism for a machine to talk to a user. Many conventional user interface devices have been well developed over the years, such as keyboard, voice recognition, touch panel, joystick, and the like. Machine interface, however, is typically limited to audible cues and visual cues.

An audible cue typically is a sound or voice initiated by a machine or a computer to notify or to respond to a user's request(s). For example, audible cues may be a beep, a voice, a ring, etc. and it is used to remind, acknowledge, and/or warn the user(s). Audible cues have been effectively used by the machines to communicate with the user(s). For example, a machine initiates a beep when a user tries to choose a menu item that is currently not available.

A visual cue typically includes a graphical cue or a textual cue enabling a machine to communicate to a user. Visual cues typically allow users to see the results of their interaction with the machine or computer immediately. For example, when a user clicks to open a file, the computer responds to user's click by providing context of the file in a text format on the display. Graphical cues typically assist and/or indicate user actions. For example, a cursor on a screen is a graphical cue to indicate or assist user action.

A problem associated with machine interface is that audible cues are not effective in certain scenarios while visual cues may not be available in some occasions. For example, a marathon runner may have a difficult time noticing visual cues via a display. Also, the runner may not be able to notice audible cues in a noisy environment.

SUMMARY

A haptic system capable of generating haptic cues in accordance with one or more detected events is disclosed. After sensing a predefined event or events via a component such as a sensor, a process of the haptic system generates an input in accordance with the sensed event. The component, for example, may include a sensor, multiple sensors, or a combination of sensors and haptic actuators. Upon receipt of the input from the component, the process retrieves a haptic signal from a tactile library in response to the input. If the sensor is a separate unit from the haptic system, a wireless network is used to transfer the information. A haptic feedback as a haptic cue in accordance with the haptic signal is generated.

Additional features and benefits of the exemplary embodiment(s) of the present invention will become apparent from the detailed description, figures and claims set forth below.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

Embodiments of the present invention are described herein in the context of a method, system and apparatus for providing haptic cues in response to one or more events using an attachable haptic device.

Those of ordinary skilled in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the exemplary embodiments of the present invention as illustrated in the accompanying drawings. The same reference indicators (or numbers) will be used throughout the drawings and the following detailed description to refer to the same or like parts.

In the interest of clarity, not all of the standard hardware and routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skilled in the art having the benefit of this disclosure.

The embodiment(s) of the present invention discloses a haptic system capable of generating a sequence of haptic cues in accordance with one or more predefined events. In one embodiment, the haptic system includes a haptic device and multiple sensors, wherein sensors and haptic actuators may be constructed in a same component. After sensing one or more events, the sensor generates an input in response to the sensed event or events and subsequently forwards the input to the haptic device. Upon receipt of the input from the sensor via a wireless network, the haptic device retrieves a haptic signal from a tactile library in accordance with the input. A haptic feedback or a sequence of haptic cues in accordance with the haptic signal is subsequently generated.

Figure 1:
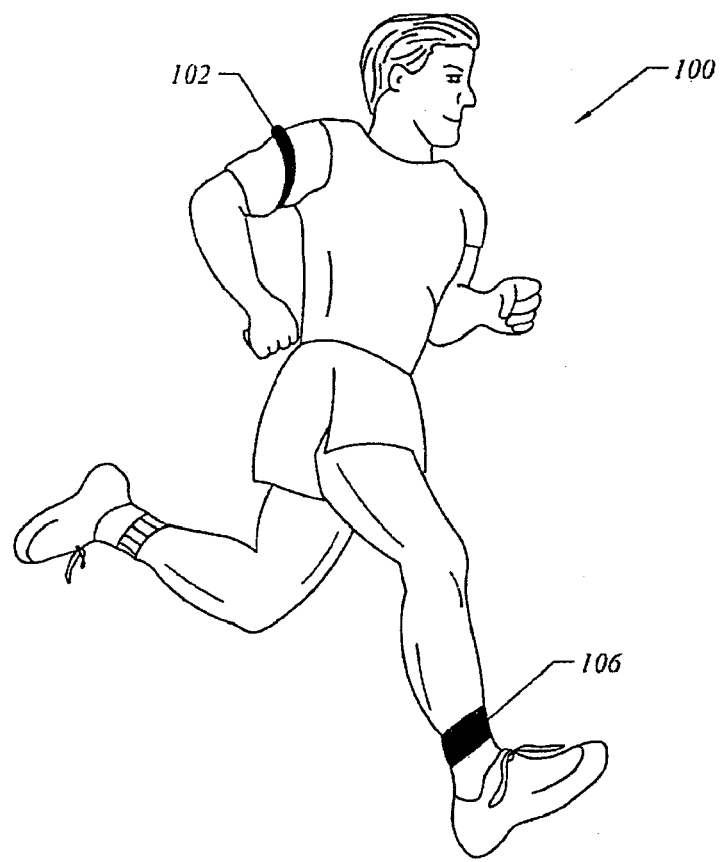
FIG. 1 is a diagram illustrating a runner wearing a haptic pacing system in accordance with one embodiment of the present invention.

FIG. 1 is a diagram 100 illustrating a runner wearing a haptic pacing system in accordance with one embodiment of the present invention. Haptic pacing system or haptic device 102 is configured to attach to the runner's arm and generates a sequence of haptic cues to pace with runner's strides. It should be noted that haptic pacing system 102 can be located anywhere on the runner's body. System 102 may include multiple sensors for detecting events. In an alternative embodiment, haptic pacing system 102 includes a separate sensing unit 106, which attaches runner's ankle sensing and collecting various runner physical condition(s), such as runner's heart rate, speed, and blood pressures. Haptic pacing system 102, in one embodiment, can be calibrated and/or configured to accommodate runner's characteristics and/or physical capabilities for optimizing runner's performance. An advantage of using the tactile pacing feedback cues is to improve athletic training efforts and performance.

A series of haptic cues, a sequence of haptic pacing sensations, or haptic feedback is generated by haptic pacing system 102 to assist or pace user's running steps. A purpose of the embodiment(s) of the invention is to enhance user's running performance in response to certain detected events. For example, a runner should improve his or her athletic performance by following a series of haptic cues. A series of haptic cues provide a range of optimal running pace for the user under the current detected physical condition(s). It should be noted that the underlying concept of the embodiment of the present invention would not change if additional devices such as sensors were added to diagram 100.

System 102 includes a sensor and an actuator, wherein the sensor and actuator may be constructed in the same device. Alternatively, system 102 includes multiple sensors and multiple haptic actuators. Sensors are used to detect conditions of the runner while actuators are used to provide haptic cues in accordance with the conditions. For example, a heart rate sensor is capable of sensing runner's heart rate while a temperature sensor measures the runner's body temperature. Detected information such as heart rate and body temperature are subsequently processed, and a series of haptic cues are generated indicating the optimal runner's pace under the currently detected information. It should be noted that the terms haptic cues, tactile cues, sequence of vibrotactile cues, and tactile cues can be used interchangeably. Also, haptic feedback can be referred to as tactile effect, tactile feedback, haptic effect, force feedback, or vibrotactile feedback.

Referring back to FIG. 1, a sensing unit 106 with multiple sensors is attached to the runner, wherein the unit 106 is logically connected to system 102 via a wireless communications network. Unit 106 may be used to detect the runner's heart rate, body temperature, ambient condition, other runners' conditions, and the like. It should be noted that system 102 may be configured to manage multiple separate sensing units 106 wherein sensors in sensing units 106 can be separately attached to the runner. A function of haptic system 102 is to provide optimal pacing mechanism to improve a runner's performance under the runner's physical as well as ambient conditions. The ambient conditions include up-hill, down-hill, weather condition, and the like. It should be noted that the feedback mechanism could be located anywhere on the body, such as in the shoe(s), on the wrist, in a helmet, etc.

The wireless communications network may include local radio frequencies, Bluetooth, cellular (GPRS, CDMA, GSM, CDPD, 2.5G, 3G, etc.), Ultra-WideBand (UWB), WiMax, ZigBee, and/or other ad-hoc/mesh wireless network technologies. To reduce power consumption, system 100 may use a relay station to amplify signal strength to conserve the power. For example, a relay station can receive haptic signals from other haptic device worn by other runners to conserve power and coverage.

System 102 can also be used in team sports such as swimmers in water polo or cyclists on a tour to identify the condition of each athlete on a team. For example, system 102 may inform one of the cyclists to speed up or slow down to improve team performance. Alternatively, system 102 can also be used to improve synchronization between athletes. It should be noted that system 102 can also be used for other applications such as assembly lines in a factory or patients in a hospital.

Figure 2:
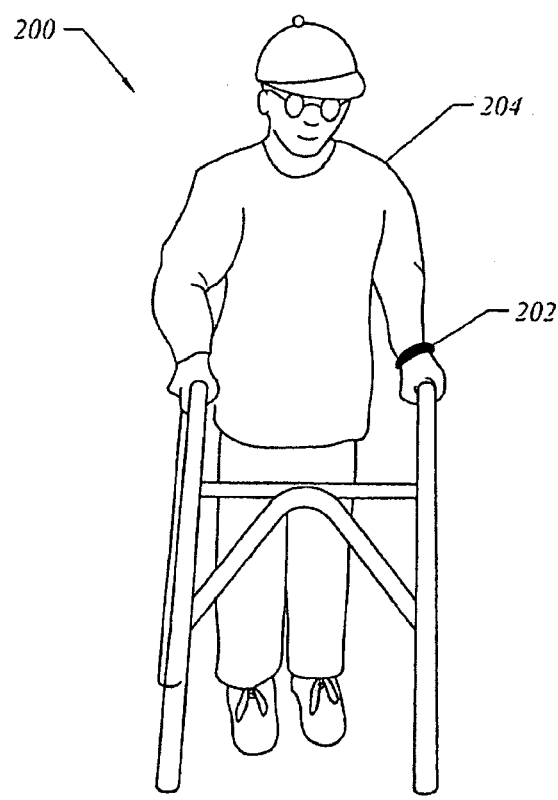
FIG. 2 is a diagram illustrating a person wearing a haptic device in accordance with one embodiment of the present invention.

FIG. 2 is a diagram 200 illustrating a person 204 wearing a haptic device 202 in accordance with one embodiment of the present invention. Haptic device 202, in one embodiment, is used by person 204 to monitor his or her physiological conditions. For example, person 204 wants to exercise but he or she needs to monitor the exertion rate. Haptic device 202, for instance, has sensors monitoring user's heart rate when he or she is exercising or walking. In addition, haptic device 202 may also measure user's body temperature on a continuous base or in a fixed time period and warn the user if his/her body temperature is in an abnormal zone. Haptic device 202 generates a haptic warning signal to warn user 204 if his or her physiological condition reaches an abnormal level. In one embodiment, haptic device 202 is capable of generating different haptic warning cues for different physical abnormalities. For example, haptic device 202 generates two different haptic cues to inform the user that his or her body temperature is normal while his or her heart rate is a little high. It should be noted that the level of abnormality can be set by a user.

Haptic device 202, in one embodiment, includes multiple sensors, wherein some sensors may be located within haptic device 202 while some sensors are separate units, which can be placed or attached to multiple locations over the body of a user. For example, a heart sensor may be placed or attached to a place closer to the heart in order to accurately detect heart conditions. Upon detecting the physical data such as heart and temperature readings, haptic device 202, for example, computes an exertion rate in response to the detected data and compares the exertion rate with a range of predefined normal exertion rates. If the exertion rate reaches to an abnormal rate, haptic device 202 generates tactile feedback to warn the user about his or her condition. Upon noticing the warning tactile feedback, user should slow down or stop doing what he or she was doing to avoid additional burden on his or her condition. It should be noted that haptic monitor can be particularly helpful for at-risk people who would like to exercise but need to monitor their health during exertion. It should be noted that some sensors may be implanted under the skin.

Haptic device 202, in one embodiment, can include multiple units wherein some of the units may be located in the chest, wrist, foot, and/or the like to generate more realistic warning signals. Haptic device 202 is capable of generating haptic cues or haptic warning signals at different levels of intensities for different levels of exertion rates. For example, haptic device 202 generates a minor haptic cue reminding the user has a slight abnormality while an intensified haptic cue warns the user that his or her physical condition is in a danger zone. Using tactile feedback to indicate the user's physiological conditions is a subtle, discreet, and non-intrusive communication method.

Haptic device 202, in another embodiment, is configured to provide subtle tactile cues for various alerts to users who want more discreet and subtle notification(s) than an overt notification(s) such as audible alarm and/or viewable lights. For example, a small haptic device 202, which can be worn or attached to any part of the user's body, is used to provide subtle haptic information without others perceiving the notification. A diabetic, for instance, may use haptic device 202, which may be incorporated into the user's watch band, capable of providing subtle vibrations to remind the user to take the insulin. Haptic device 202 can also be useful for elderly persons who may have trouble remembering things but would want to be reminded in a more subtle manner. In an alternative scenario, a parent, who is in a meeting, may receive a subtle notification from haptic device 202 indicating his or her child is home/not home without interrupting the meeting. It should be noted that haptic devices 202 can be incorporated into everyday things such as clothing, glasses, and belts.

Figure 3:
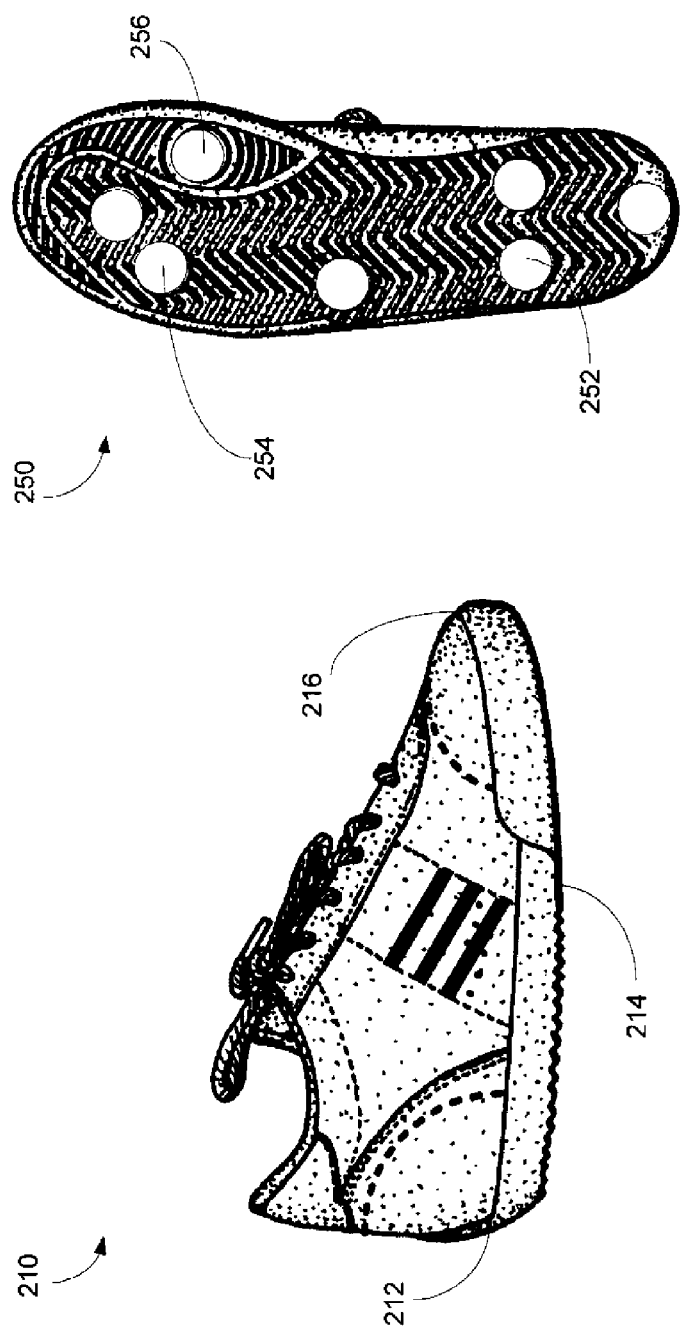
FIG. 3 illustrates a diagram showing a haptic shoe capable of correcting strides relating to abnormalities in accordance with one embodiment of the present invention.

FIG. 3 illustrates a diagram 210 showing a shoe having a haptic device capable of correcting strides related abnormalities in accordance with one embodiment of the present invention. In one embodiment, the shoe includes a front sensor 216, a back sensor 212, and a sole sensor 214. Sensors 212-216 are used to detect strides related abnormalities associated with the user. It should be noted that the underlying concept of the embodiment of the present invention would not change if additional sensors or devices were added to or removed from the shoe.

Diagram 250 illustrates a sole of the shoe having various sensors 252-256 used for analyzing the user's stride. For example, sensor 252 is used to sense the weight exerted on the back right-hand side of the sole while sensor 256 is used to detect the pressure exerted on the front left-hand side of the sole. From the data collected from sensors 252-256, haptic device associated with the shoe is capable of identifying the abnormalities associated with the user's strides. In an alternative embodiment, the haptic device associated with the shoe is capable of providing tactile feedback to assist in correcting the abnormalities in real-time. For example, sensor 254, which is also a haptic actuator, generates a tactile cue when it detects an abnormal amount of exertion on the front right-hand side of the sole.

A small haptic mechanism incorporated in a pair of running (or training) shoes may be used to provide haptic cues to the user to improve specific elements of running such as strides. To correct stride abnormalities, the haptic device can provide immediate tactile feedback to the user indicating the location of the abnormalities. For example, the shoe could vibrate with greater intensity if the person is putting too much weight on the outside of the shoe or bringing his heel down too forcefully. The exemplary embodiment of the present invention can also be applied to medically disabled patients such as cerebral palsy patients who need assistance to improve their walk.

It should be noted that sensors and haptic actuators can be the same device. It should be further noted that vibrotactile feedback or haptic feedback may be provided through a piezo materials, shape memory alloy ("SMA"), eccentric rotating mass ("ERM") or linear resonant actuator ("LRA"), or the like. Piezoelectric material, in one embodiment, may be used to construct a sensor and actuator device.

Some materials such as piezoelectric material have the physical property of sensing as well as providing vibrotactile effect. For example, piezoelectric material discharges a current indicating it detected a pressure when its physical shape deforms due to a pressure. The dimension of piezoelectric material can be reduced to a relatively small size such as 5 millimeters by 5 millimeters. Piezoelectric materials, in one embodiment, include crystals and/or ceramics such as quartz ($SiO_2$). When a voltage potential applies to the piezoelectric material, it deforms from its original shape to an expanded shape. Piezoelectric material may return to its original state as soon as the voltage potential is removed. Piezoelectric material, however, releases a current when it is being pressed. As a result, piezoelectric material can detect an input when it is being pressed. Similar functions of sensor/actuator may be performed if the piezoelectric material is replaced with other devices such as LRA, ERM, and SMA, wherein SMA, for example, is capable of maintaining its deformed shape for a period of time after the voltage potential is removed. It should be noted that the underlying concept of the embodiments of the present invention does not change if different materials other than piezoelectric actuators are employed.

Figure 4:
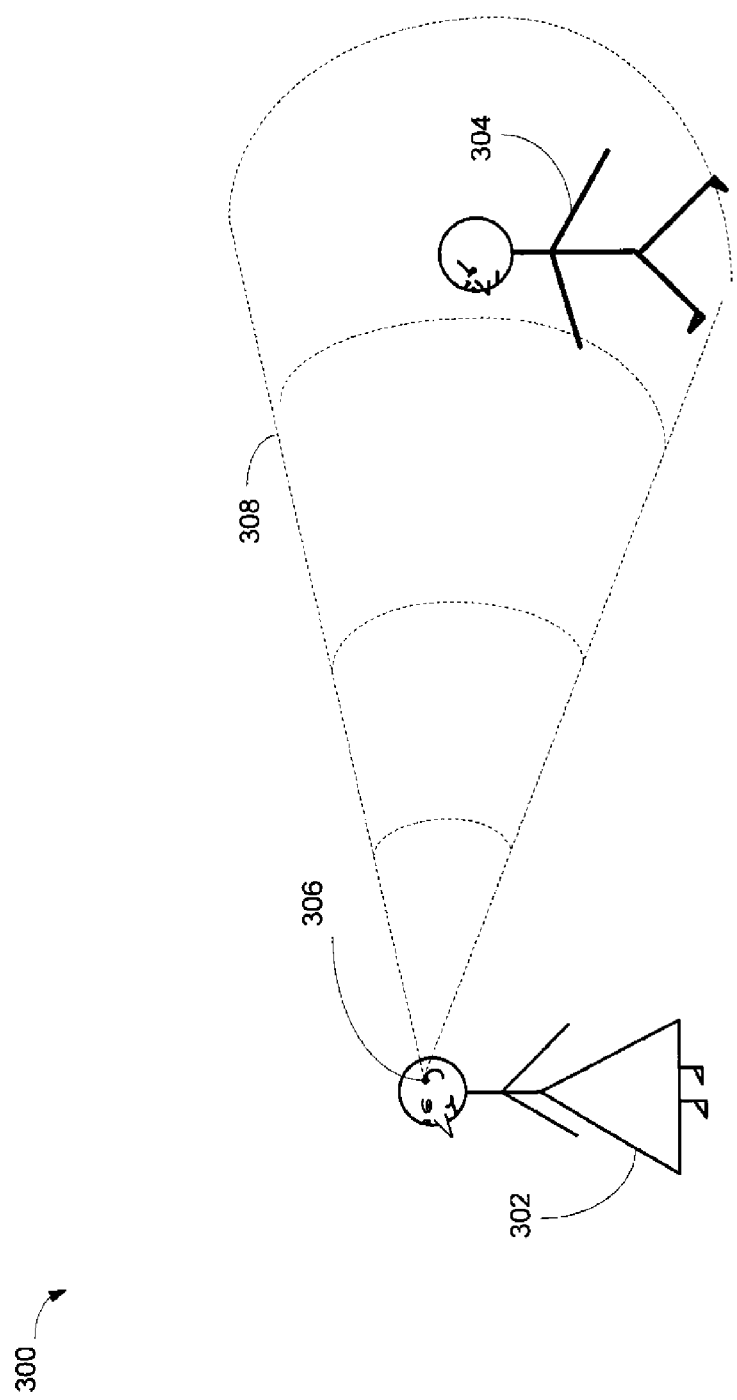
FIG. 4 is a diagram illustrating a person wearing a haptic ambient warning device capable of detecting moving object in accordance with one embodiment of the present invention.

FIG. 4 is a block diagram 300 illustrating a woman 302 wearing a haptic ambient warning device 306 capable of detecting moving object(s) in accordance with one embodiment of the present invention. Haptic ambient warning device 306 is configured to selectively generate haptic warning cues when one or more moving objects are detected in the surrounding environment. For example, haptic wearable device 306, which provides tactile cues to the head, neck or shoulder, generates haptic alert or alerts to user 302 if it detects a vehicle or a person 304 in the ambient environment and approaching quickly to the user.

In another embodiment, haptic wearable device 306 is capable of emulating a natural human response or natural feelings such as "hair raising on the back of the neck" physiological response to potential danger. Natural human response means a person's natural reaction when he or she senses certain excitements or dangers. The expression of "hair raising on the back of the neck" indicates a natural and curious phenomenon. The movement of hair on the back of the neck is generally involuntary. When you experience something that causes the hair active, which you don't have any control, you just have that feeling that you're in the middle of something exciting. It should be noted that multiple actuators may be used to emulate a natural realistic sensation.

Haptic device 306 can also be used by a driver to monitor ambient environment for traffic situations. For example, haptic device can provide warning information indicating that someone is passing them too fast or some vehicles present on blind spots. It should be noted that haptic wearable warning device is applicable to various situations such as runners, walkers, bicyclists, motorcyclists, and the like. It should be further noted that haptic wearable device 306 may include a calibrator, which initializes or calibrates haptic wearable device 306 to specific arrange of applications. The calibrator may be controlled by the user or by a machine located remotely via wireless communications network.

The exemplary embodiment(s) of the present invention includes various processing steps, which will be described below. The steps of the embodiments may be embodied in machine or computer executable instructions. The instructions can be used to cause a general purpose or special purpose system, which is programmed with the instructions, to perform the steps of the present invention. Alternatively, the steps of the present invention may be performed by specific hardware components that contain hard-wired logic for performing the steps, or by any combination of programmed computer components and custom hardware components. While embodiments of the present invention will be described with reference to the Internet, the method and apparatus described herein is equally applicable to other network infrastructures or other data communications environments.

Figure 5:
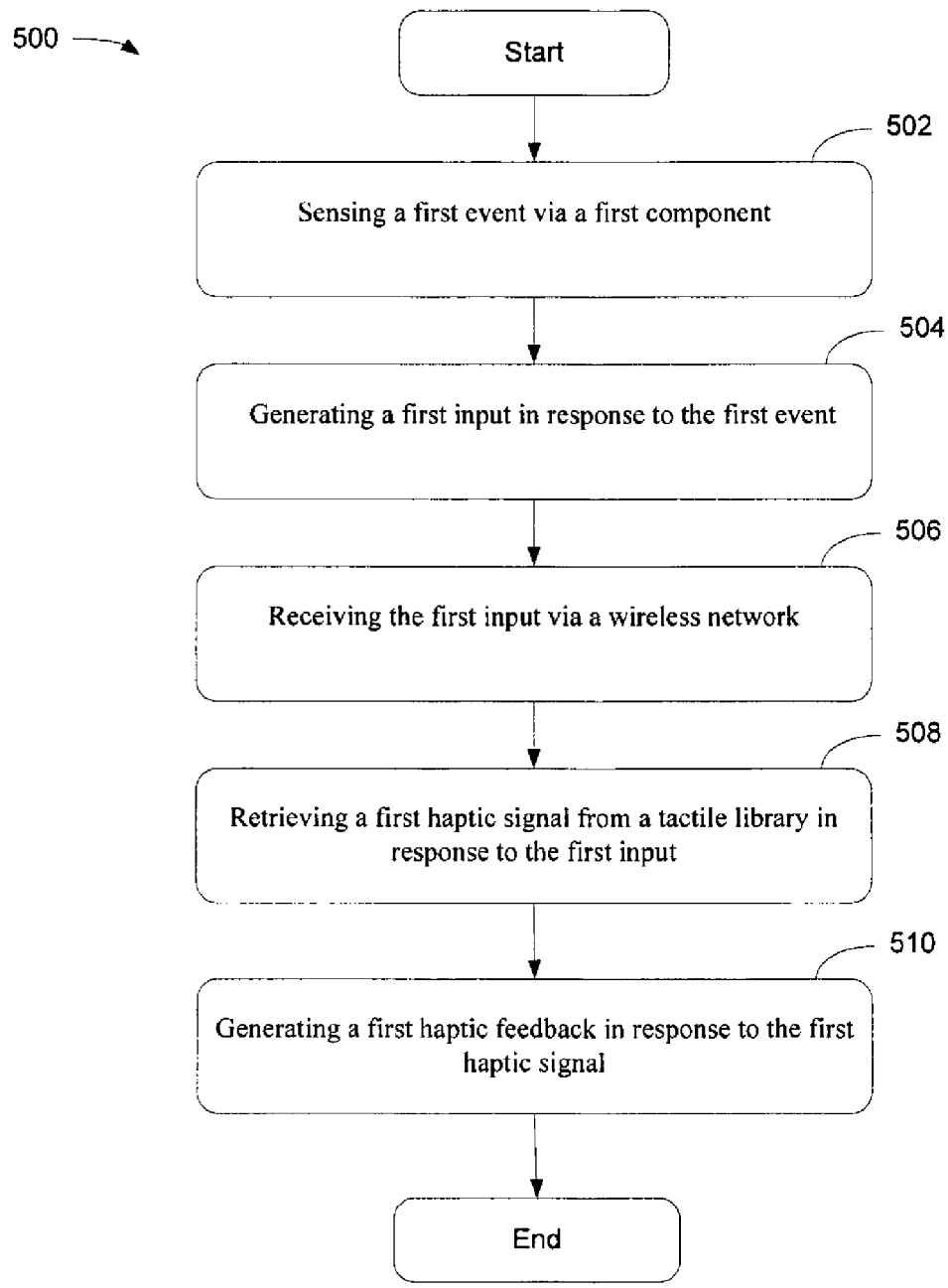
FIG. 5 is a flowchart illustrating a process of providing haptic cues in response to one or more events in accordance with one embodiment of the present invention.

FIG. 5 is a flowchart illustrating a process of providing haptic cues in response to one or more events in accordance with one embodiment of the present invention. At block 502, the process senses a first event via a first component. The first event could be a heart rate, body temperature, a movement, and the like. The first component could be a sensor capable of detecting a heart rate. The process, for example, may detect a predefined movement, which occurs from a distant location or a nearby location. Upon detecting a moving object, the process calculates the speed and direction of the moving object and generates a haptic warning signal in response to the moving object. In one embodiment, the process is capable of providing an urgent haptic alert if the moving object is approaching quickly. Alternatively, the process generates a haptic warning that a moving object is passing by. If the sensor and haptic device are separate units, wireless communications network may be needed to logically connect the units together. After block 502, the process proceeds to the next block.

At block 504, upon sensing the first event, the process generates a first input in response to the first event. For example, when a sensor detects a heart rate from the user, the sensor converts the heart rate information to an input in a communication network protocol. If the sensor is a separate unit from the haptic device, the sensor transmits the input signal to the haptic device via a communication means. For example, a wireless communication network is used to transmit information between the sensor and the haptic device. The sensor, for instance, may be attached to the chest of a user and the haptic device may be worn on the wrist. After block 504, the process proceeds to the next block.

At block 506, the process receives the first input via a wireless network. It should be noted that if the sensor and the haptic device are constructed on the same unit, wireless communications network is not required. After block 506, the process moves to the next block.

At block 508, upon receipt of the first input, the process retrieves a first haptic signal from a tactile library. In one embodiment, the tactile library includes multiple haptic signals wherein each haptic signal indicates a specific type of tactile cues to be generated. The tactile library, in one embodiment, is a predefined table that can be updated by a user or a remote server. After block 508, the process moves to the next block.

At block 510, the process generates a first haptic feedback in response to the first haptic signal. In one embodiment, upon sensing a second event via a second component, the process generates a second input in response to the second event. After receiving the second input via the wireless communications network, the process retrieves a second haptic signal from the tactile library in response to the first input and the second input. A second haptic feedback in response to the second haptic signal is subsequently generated by the haptic device. For example, the process is capable of detecting a heart rate as well as a body temperature. Alternatively, the process is further capable of computing a speed of pacing in response to the heart rate and the body temperature, and subsequently fetching a haptic pacing sequence from the tactile library in response to the speed of pacing. It should be noted that producing a sequence of haptic feedback further includes activating the first component to generating the sequence of haptic feedback. In another embodiment, the process is capable of generating haptic feedback emulating natural sensations in response to a moving object. After block 510, the process ends.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope all such changes and modifications as are within the true spirit and scope of the exemplary embodiment(s) of is present invention.

What is claimed is:

1. A system for generating haptic signals, comprising:
a sensor configured to:
detect a condition, wherein the condition is associated with a speed of a moving object detected by the sensor;
generate an input based on the condition; and
transmit the input; and
a haptic device logically coupled to the sensor, the haptic device configured to:
receive the input; and
generate a haptic feedback based on the input, wherein an intensity of the haptic feedback varies based on the speed associated with the condition.

2. The system of claim 1, wherein the sensor is configured to be attachable to a body.

3. The system of claim 1, wherein the condition comprises a physical condition.

4. The system of claim 1, wherein the haptic feedback comprises a haptic pacing sequence.

5. The system of claim 4, further comprising a second sensor logically coupled to the sensor, wherein the second sensor is configured to detect a body temperature and wherein the second sensor is configured to generate a second input based on the body temperature.

6. The system of claim 5, wherein the haptic device is configured to receive the second input via a wireless communications network and generate a second haptic pacing sequence based on the first input and the second input.

7. The system of claim 5, wherein the second sensor is configured to be attachable to a body.

8. The system of claim 1, wherein the sensor is configured to be attachable to a wearable object to be worn by a user.

9. The system of claim 8, wherein the condition comprises a strain associated with the wearable object.

10. The system of claim 9, wherein the strain is associated with an abnormal posture of the user.

11. The system of claim 9, wherein the wearable object comprises a shoe and wherein the strain associated with the wearable object comprises a pressure exerted on the shoe.

12. The system of claim 9, wherein the wearable object comprises a glove and wherein the strain associated with the wearable object comprises a pressure exerted on the glove.

13. The system of claim 1, wherein the sensor and the haptic device are housed in a single device.

14. The system of claim 1, wherein the haptic device further comprises a selector.

15. The system of claim 14, wherein the selector chooses the intensity of the haptic feedback based on the condition.

16. The system of claim 15, wherein the condition is associated with an abnormality of a posture of a user.

17. The system of claim 1, wherein the haptic device is configured to be attachable to a body.

18. The system of claim 1, wherein the condition is further associated with a direction of the moving object in an environment.

19. The system of claim 18, wherein the sensor is configured to track a plurality of moving objects at substantially the same time.

20. The system of claim 18, wherein the moving object comprises a vehicle, a person, or an animal.

21. The system of claim 1, wherein the haptic feedback comprises an emulation of a natural feeling of a predictable event in an environment.

22. The system of claim 1, wherein the haptic feedback indicates a danger.

23. The system of claim 1, wherein the haptic feedback indicates a safe condition.

24. A method for generating haptic signals, comprising:
   detecting, by a sensor, a condition, wherein the condition is associated with a speed of a moving object detected by the sensor;
   generating, by the sensor, an input based on the speed associated with the condition;
   transmitting, by the sensor, the input;
   receiving, by a haptic device that is logically coupled to the sensor, the input; and
   generating, by the haptic device, haptic feedback based on the input, wherein an intensity of the haptic feedback varies based on the speed associated with the condition.

25. The system of claim 1, wherein the sensor is configured to be implanted under a skin of a user of the system.

26. The system of claim 11, wherein the sensor is configured to detect the pressure exerted on the shoe at a first side of the shoe.

27. The system of claim 26, further comprising:
   a second sensor configured to detect a pressure exerted on the shoe at a second side of the shoe.

28. The system of claim 26, further comprising:
   a second sensor configured to detect a weight at a second side of the shoe.

29. The system of claim 9, wherein the strain is associated with an abnormal stride of a user.

30. The system of claim 29, wherein the haptic feedback indicates a location of an abnormal pressure exerted on the shoe.

31. The system of claim 9, wherein the haptic feedback indicates a location of an abnormal strain on the wearable object.

32. The system of claim 1, wherein the sensor comprises a haptic actuator.

33. The system of claim 18, wherein the sensor is configured to monitor an ambient environment for traffic situations.

34. The system of claim 33, wherein the haptic device indicates warning information regarding driving conditions.

35. The system of claim 33, wherein the haptic device indicates whether a vehicle is in a blind spot.

* * * * *